United States Patent [19]

Zeineh

[11] 4,025,200
[45] May 24, 1977

[54] SOFT AND LINE LASER

[76] Inventor: Rashid A. Zeineh, 5742 W. Dakin St., Chicago, Ill. 60634

[22] Filed: Feb. 3, 1975

[21] Appl. No.: 546,513

[52] U.S. Cl. .............................................. 356/201
[51] Int. Cl.² ......................................... G01N 21/06
[58] Field of Search ......... 331/94.5; 350/190, 96 B; 356/111, 201

[56] References Cited

UNITED STATES PATENTS

| | | | |
|---|---|---|---|
| 2,980,802 | 4/1961 | Bracey et al. | 350/190 |
| 3,788,748 | 1/1974 | Knight et al. | 350/190 |
| 3,843,261 | 10/1974 | Pryor | 356/111 |

*Primary Examiner*—William L. Sikes
*Attorney, Agent, or Firm*—McWilliams & Mann

[57] ABSTRACT

An arrangement for using laser light in densitometers and spectrophotometers by using filters to cut down intensity and variable slits to regulate sensitivity. The arrangement also contemplates stretching the spot laser to a line laser by using a hollow transparent tubing in front of the laser and moving it to obtain various intensities. The line laser may be focused by a cylindrical lens at a fixed position, and the beam width may be adjusted by moving a cylindrical lens away or closer to the sample object. Furthermore, a slit before the sample and a slit after the sample will improve resolution by cutting off diffracted or aberated light.

5 Claims, 9 Drawing Figures

U.S. Patent  May 24, 1977  4,025,200
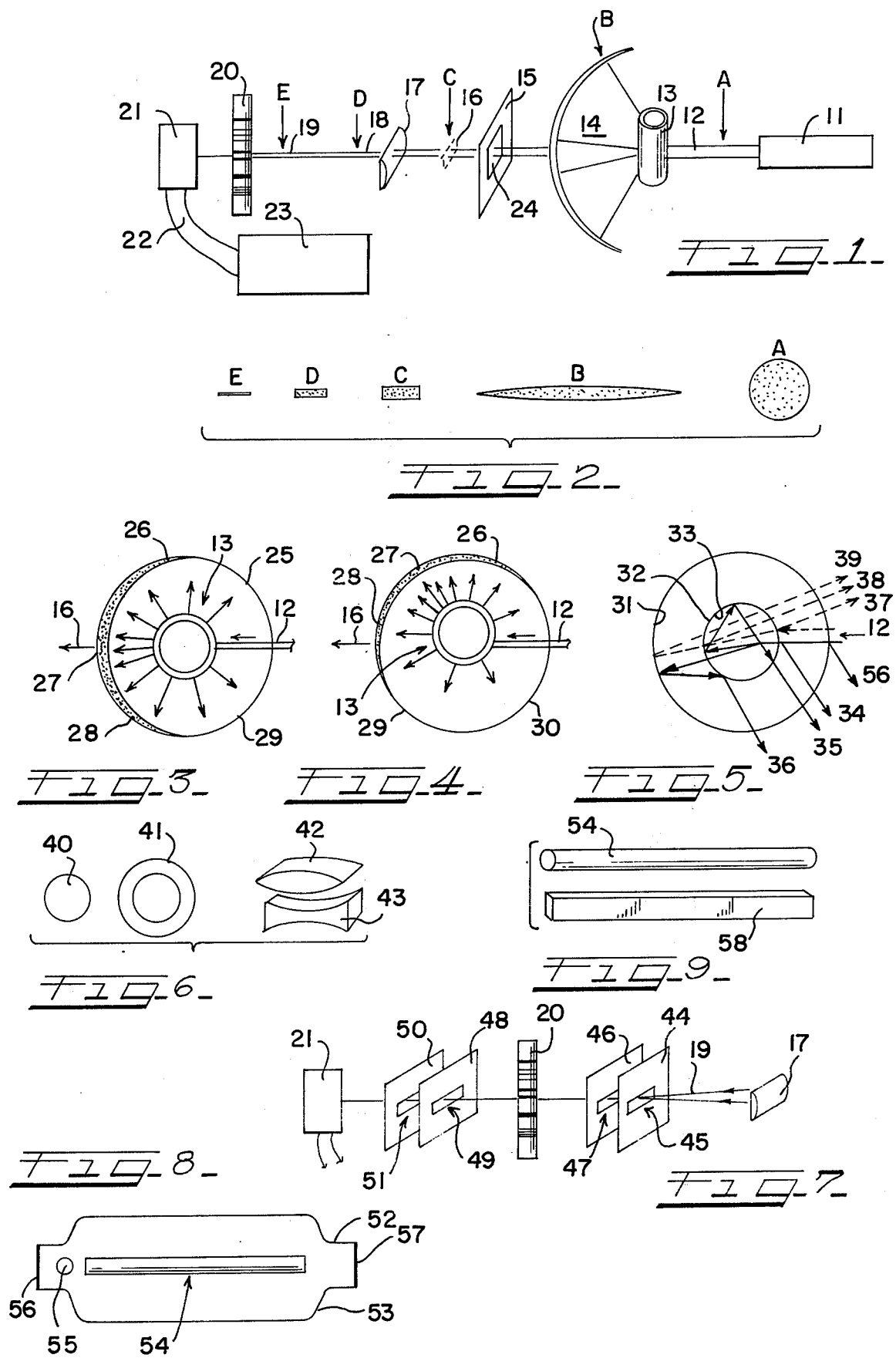

SOFT AND LINE LASER

BACKGROUND OF THE INVENTION

The present invention relates to the production of soft laser light and line laser light, and their uses in various fields. One major field of use is spectrophotometers and scanning densitometers. Other uses are communication, detection, photography, microscopy, movies and television and others. The major one particular use is scanning densitometry where high resolution and sensitivity are improved by using the soft and/or line laser.

Methods of protein separation have improved greatly while quantitation by densitometry has lagged behind. Disc electrophoresis on polyacrylamide gel achieves a high resolution that could be qualitatively observed but no available scanning densitometer can do the pattern recording. Bands appearing separated by visual observation reveals overlapping peaks. The resolution obtained on gel is partially or significantly lost upon scanning. The complex pattern obtained by isoelectric focusing calls for further improvement of scanners resolution. ICEP has further increased the requirement of higher resolution.

Disc electrophoresis needs scanning densitometers of $100\mu$ resolution. Isoelectric focusing on polyacrylamide gel needs $50\mu$ resolution and so does ICEP. In order to make isoelectric focusing scannable by present instruments LKB Company, the inventors, changed to sheet rather than tube isoelectric focusing. Upon drying, the bands of separated proteins by isoelectric focusing plate, shrink to a thin film and scanning has less chance to lose resolution. But still the pattern is very complex and regular light scanning densitometry still loses the resolution which could be seen by the naked eye.

An attractive present trend to improve resolution is to use the microscope system in order to detect transmitted light through narrow areas but light diffraction made this system of very limited use. The resolution is improved slightly, but the background noise is increased.

The most successful system so far is to take a picture and scan the transparent negative film with double microscope system. One lens system focuses the light and converges it to a spot at the plane of the negative. The second miscroscope detects and quantitates the transmitted light through the spot, not the diffracted portion, and focuses it on a photodetector. This is a very tedious and time consuming process. The resolution is still lost (a) during picture taking, where focusing is on a limited area only and (b) diffraction and scattering of regular light still imposes the limited resolution.

Another approach is the photon counting system in which a narrow slit lowers the light intensity, and this is accompanied by less diffraction. The background noise increases and the stained protein bands are relatively too dark. Thus, Beer's law does not hold for optical density quantitation.

OBJECTS OF THE INVENTION

The major objective of this invention is to produce a line laser by stretching the light from a spot laser source using a hollow transparent tubing such as glass, quartz, plexiglass, plastics, and others. Solid rods or cylindrical lenses of these materials also stretch the spot laser to a line laser. The line laser, in fact, is a long line comprised of many spots.

Another object is to produce a line laser of variable intensity by moving the tubing in a plane vertical to the incident beam of the spot laser. If the laser passes through the center of the tubing, maximal intensity of stretched light goes through and remains in a straight direction. When the tubing is moved and the spot laser hits the sides of the tubing, a lower intensity beam of stretched laser goes through straight. The further the spot laser hits the tubing from the center of the tube, the lower the intensity of the stretched laser goes through straight and the width of the beam becomes smaller. When the spot laser does not hit the tubing at all, it remains as a spot laser. Then a variable slit could be used to change the intensity of light transmitted through the sample for optical density determinations.

Another object is to produce a line laser with narrow beam width by using a hollow transparent tubing technique.

Another object is to obtain a minimal width of laser light beam by using a cylindrical lens whose axis and focal point are in the same plane as the line laser and whose distance from the sample is equal to its focal length.

Another object is to produce a line laser at various intensities by using the transparent tubing technique and by changing the beam width with a cylindrical lens, whose distance from the object is variable; as by mounting the cylindrical lens on a rack and pinion arrangement. Turning the pinion will move the lens to adjust the beam width of the line laser.

Another object is to use a before the sample slit or a double slit which is primarily to cut off the aberated and diffracted portion of the light beam and thus produce a light beam with straight edges.

Another object is to use a before the sample slit to control the width of the line laser beam whether the cylindrical lens is used or omitted. The beam of laser light produced by using the before the sample slit, could be narrower than the beam from the regular light source. Using a regular light source, there is a limitation by diffraction and interference to the smallest beam width obtainable.

Another object is to use a slit after or behind the sample in order to allow the straight transmitted light only to reach the photodetector or the photo sensor in the densitometer.

Another object is to use a before the sample slit and another slit after the sample for better resolution.

Another object is that the slit is a double slit in structure so that only the parallel light can go through.

Another object is to produce a line laser which is stretched by single or multiple tubing technique, or by a cylindrical lens to replace the spot laser for screening the skies, sea, or land in a concept, parallel to radar or sonar detectors with the advantage of greater accuracy. Also, one sweep is needed with a line laser instead of very many sweeps of a spot laser for that purpose.

Another object is to use the line laser in copying machines for finer and improved copy making.

Another object is to use the line laser for movie production where the pictures would be of higher quality, better precision, and a greater concept of depth. The three dimensional concept is improved.

Another object is to use the line laser for magnifiers as in the process of printing pictures where there is no need for focusing, or lens arrangement and magnification is changed by changing the distance.

Another object is the use of a line laser in communication. The line laser is indeed a long row of spot lasers that are produced by the tubing technique. Each individual spot could carry a telephone connection, and the permutation and various combinations of these multiple spot lasers or line lasers could improve the long-distance telephone connections manyfold. For example, the number of long-distance calls will be increased ten thousand fold or more over the present system where regular light waves of electro-magnetic sources are used. Another improvement is in the quality of phone connections. They will be significantly increased, especially when television-phone combination is used.

Another object is to use the line laser in television systems where the picture as well as the sound could be improved.

BRIEF DESCRIPTION OF THE DRAWINGS

FIG. 1 illustrates the basic arrangement of the line laser of controlled intensity and adjustable width.

FIG. 2 is a cross section of the laser beam in FIG. 1 at positions A—A, B—B, C—C, D—D, E—E.

FIG. 3 illustrates a basic method of producing the line laser beam from a spot laser beam.

FIG. 4 illustrates an adjustment of the laser beam intensity and width by varying the position of the glass tubing.

FIG. 5 illustrates the path ways and distribution methods of the spot laser beam incident to the glass tubing.

FIG. 6 illustrates the various glass components that could be utilized to produce a line laser.

FIG. 7 illustrates the use of a double slit system before and after the object to be scanned in order to remove abberation and distortion of the laser beam and prevent them from reaching the photodetector.

FIG. 8 illustrates a built in glass tubing in the gas laser tube; and

FIG. 9 illustrates the production of a line laser beam by using a rectangular glass tubing instead of a circular tube in the laser gas tube.

DETAILED DESCRIPTION OF THE INVENTION

With specific reference to the drawings and referring to FIG. 1, the basis of utilizing laser light for densitometry and spectrophotometry is illustrated. The laser source 11 emits a spot laser beam 12 which is intercepted by a clear tubing 13 made of glass or any other transparent or semitransparent material. The emerging beam 14 is elongated and has various thicknesses in cross sections. The plate 15 with opening 24 permits a segment of the beam 16 to reach a cylindrical lens (or cylindrical mirror) 17. The penetrating beam 18 is compressed in width at a position closer to the lens, another beam 18 later is compressed further at position 19 at the proximity of the object 20 to be scanned. The penetrating focused beam passing through the object is detected by photodetector 21 and is relayed to the monitoring system 23 through conduit 22. The monitoring system 23 may include a chart recorder, integrator, computer print out, metering devices, or other systems for quantitation and scanning of the object 20. The object 20 can be an electrophoregram, a separation system of cuvette to hold solutions.

FIG. 2 illustrates the changes of the spot laser beam to a line laser beam. The original laser beam of a spot shape 12 is a cross section of the original incident beam. This cross section A—A is taken from FIG. 7. The cross section B—B in FIG. 1 is seen as an elongated line laser B, thick at the center and decreased in width as you get away from the center. The cross section C—C in FIG. 1 shows a segment of C of the laser beam B. The beam segment C incident to the cylindrical lens 17 FIG. 1 is compressed in width. At the position D—D cross section the laser beam is compressed slightly and appears as D in cross section. At a position closer to the object the cross section E—E of the focused beam is further compressed to a smaller width and appears as E. The beam is theoretically focused at the object and has minimal width. Changing the position of the cylindrical lens 17 or moving it towards the object modifies the width of the beam E incident to the object so that the beam width gets larger and resolution is decreased while sensitivity may be increased.

FIG. 3 illustrates the production of a line laser from the spot laser beam 12 incident to the tubing 13. Through internal reflection and probably some diffraction the emerging laser beam goes in all directions and spreads over 360° around tubing 13. When the spot laser beam 12 is incident to the center of the tubing (which is perpendicular to the incident beam) the emerging beam 16 is thickest and widest in the same direction as the original spot laser beam 12. At position 27 the emerging beam is thickest and most intense. At position 26 and 28 on either side the beam gets thinner. At positions 25 and 29 it becomes even more thin.

FIG. 4 illustrates the production of the line laser segment with different intensity and width. By moving the hollow glass tubing to the side, the spot laser beam 12 will be incident to the side of the hollow transparent tubing and the complex process of reflection at the various interfaces between glass and air results in shifting the distribution of laser light as seen in FIG. 4. All the distribution appears to be shifted in the clock wise direction as in FIG. 4 and the emerging straight laser segment 16 which is in the same direction and continuation of the original beam 12. In FIG. 4 the segment of the line laser that passes through the cylindrical lens is segment 28 which is less in intensity and width than the passing segment 27 in FIG. 3. This illustrates that by moving the hollow transparent tubing the segment of line laser that goes through the cylindrical lens is selected. When the hollow tubing is not in the way of the spot laser then the original laser beam 12 will be focused by the cylindrical lens to a form of elongated oval shape of minimal intensity for scanning.

FIG. 5 illustrates the internal reflection of the laser beam. The emerging light will be distributed as in FIG. 4. Selected representative direction of the emerging beam is shown to illustrate the laser line produced. The emerging laser is composed of various combinations of reflection. The first beam 56 is reflected from the outer surface. The beam 34 is reflected once from the inside surface of the inner interface. Beam 36 is reflected first from the inner surface 31 of the outer interface and again reflected from the outer surface of the inner interface. Similarly beams 37, 38, 39, in the same direction are reflected from the outer surface of the inner interface 32, inner surface of the inner interface 33, and the inner intersurface of the outer interface 31 respectively.

FIG. 6 illustrates various forms of transparent objects that could be used to stretch the spot laser to a line laser. A round rod 40, hollow tubing 41, cylindrical lens 42 and cylindrical lens 43, could be used to produce the line laser from the original spot laser. The curvature of each component 40, 41, 42, or 43 influences the distribution of the line laser produced.

FIG. 7 illustrates the use of double slit system before and after the object to be scanned in order to obtain final resolution by obstructing the aberated and distorted light and to allow the parallel straight beam that goes through the object to reach the photodetector.

FIG. 8 illustrates the production of a line laser directly from a laser gas tube. A hollow transparent tubing 55 is inserted in front of the mirror 56 where most of the laser beam emerges. The electrical voltage or potential is connected to terminals 52 and 53. Mirror 57 has very low transmission and little amount of laser light penetrates through it. The mirror on the other end 56 allows the majority of the laser light to pass through after being collected by the internal tubing 54 and stretched by a small segment of transparent tubing 55 or the equivalent. The mirrors on either end of the laser tube could be cylindrical and thus producing a line laser without the insert tubing 55.

FIG. 9 illustrates the production of line laser by using a rectangular inner tubing 58 instead of the circular inner tubing 54 of FIG. 8. The emerging beam will have the same shape as the rectangular hollow tubing center. In this case the hollow space is a rectangular of 2 long sides and two short ones. Thus the emerging laser beam is long and slim.

What is claimed is:

1. A soft laser densitometer comprising a light source emitting a laser beam, a cylindrical transparent member adapted to stretch said laser beam in a plane perpendicular to the cylindrical member, an opaque member in the path of the stretched beam disposed perpendicular thereto and having an opening adapted to pass a segment of said stretched beam through the opaque member, a cylindrical lens of positive focal length in the path of said segment of the stretched beam, the axis of said lens being in the same plane as said stretched beam and perpendicular to said cylindrical member, said cylindrical lens focusing said segment on an object to be scanned, and said segment having minimum width and variable length, said object containing separated bands for analysis and the plane of the focused segment being parallel with the plane of said separate bands, a photodetector behind said object adapted to detect transmitted light through said object or to the side thereof to detect flourescence or reflection, and a carriage for mounting said object adapted to have translational movement in a direction perpendicular to said segment, said photodetector providing an electrical signal to a chart recorder or computor to pattern analysis.

2. A soft laser densitometer as set forth in claim 1 wherein said lens is fixed to a mount which moves forward and back in the path of said segment and such movement adjusts the width of said segment incident to said object.

3. A soft laser densitometer as set forth in claim 1 wherein a slit is located in the path of said beam before the light beam reaches said object.

4. A soft laser densitometer as set forth in claim 3 wherein a slit is located in the path of said segment after said object.

5. A soft laser densitometer as set forth in claim 1 wherein said cylindrical transparent member is fixed to a movable mount the motions of which is perpendicular to the laser beam and perpendicular to the axis of the cylindrical member, said motion of the cylindrical member on said mount being adapted to adjust the intensity of the laser beam.

* * * * *